(12) United States Patent
Mansfield

(10) Patent No.: US 8,795,809 B2
(45) Date of Patent: *Aug. 5, 2014

(54) TEAR RESISTANT FILM

(75) Inventor: Todd Leon Mansfield, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 533 days.

This patent is subject to a terminal disclaimer.

(21) Appl. No.: 13/026,533

(22) Filed: Feb. 14, 2011

(65) Prior Publication Data

US 2012/0207969 A1  Aug. 16, 2012

(51) Int. Cl.
| | |
|---|---|
| C08L 53/02 | (2006.01) |
| C08F 8/04 | (2006.01) |
| C08F 297/04 | (2006.01) |
| A61L 15/26 | (2006.01) |
| B32B 3/24 | (2006.01) |

(52) U.S. Cl.
USPC ............ 428/131; 428/219; 523/122; 525/98; 525/314

(58) Field of Classification Search
None
See application file for complete search history.

(56) References Cited

U.S. PATENT DOCUMENTS

| | | | |
|---|---|---|---|
| 3,806,003 A | 4/1974 | Fujimoto | |
| 3,929,135 A | 12/1975 | Thompson | |
| 4,151,240 A | 4/1979 | Lucas et al. | |
| 4,243,314 A | 1/1981 | Bowe et al. | |
| 4,324,246 A | 4/1982 | Mullane et al. | |
| 4,463,045 A | 7/1984 | Ahr et al. | |
| 4,552,709 A | 11/1985 | Koger, II et al. | |
| 4,591,523 A | 5/1986 | Thompson | |
| 4,808,178 A | 2/1989 | Aziz et al. | |
| 4,909,803 A | 3/1990 | Aziz et al. | |
| 5,151,092 A | 9/1992 | Buell et al. | |
| 5,221,274 A | 6/1993 | Buell et al. | |
| 5,278,220 A * | 1/1994 | Vermeire et al. | 524/490 |
| 5,336,554 A * | 8/1994 | Knight | 428/137 |
| 5,554,145 A | 9/1996 | Roe et al. | |
| 5,569,234 A | 10/1996 | Buell et al. | |
| 5,580,411 A | 12/1996 | Nease et al. | |
| 5,885,908 A | 3/1999 | Jaeger et al. | |
| 6,004,306 A | 12/1999 | Robles et al. | |
| 6,120,487 A | 9/2000 | Ashton | |
| 6,148,830 A * | 11/2000 | Chen | 132/321 |
| 6,410,129 B2 * | 6/2002 | Zhang et al. | 428/318.6 |
| 6,472,084 B1 | 10/2002 | Middlesworth et al. | |
| 7,307,031 B2 | 12/2007 | Carroll et al. | |
| 7,626,073 B2 | 12/2009 | Catalan | |
| 8,551,896 B2 * | 10/2013 | Mansfield | 442/398 |
| 2002/0001707 A1 * | 1/2002 | Zhang et al. | 428/318.6 |
| 2002/0182371 A1 * | 12/2002 | Soon et al. | 428/137 |
| 2003/0022582 A1 * | 1/2003 | Cree et al. | 442/394 |

(Continued)

OTHER PUBLICATIONS

PCT International Search Report mailed May 11, 2012 (8 pages).
U.S. Appl. No. 13/026,548, filed Feb. 14, 2011, Todd Leon Mansfield.
U.S. Appl. No. 13/026,563, filed Feb. 14, 2011, Todd Leon Mansfield.

*Primary Examiner* — Aaron Austin
*Assistant Examiner* — Jeff Vonch
(74) *Attorney, Agent, or Firm* — Laura L. Whitmer; John G. Powell

(57) ABSTRACT

An elastic film material that resists the propagation of a tear. The film material includes an SEEPS elastomeric block copolymer and has a time to break of at least 10 hours. The elastomeric block copolymer has a $T_m$ of between about 10° C. and 20° C.

19 Claims, 10 Drawing Sheets

(56) References Cited

U.S. PATENT DOCUMENTS

| | | |
|---|---|---|
| 2005/0222331 A1 | 10/2005 | Hoshi et al. |
| 2005/0273072 A1* | 12/2005 | Hird et al. ................ 604/385.24 |
| 2007/0066753 A1* | 3/2007 | Ehrlich et al. .................. 525/89 |
| 2007/0073256 A1 | 3/2007 | Ponomarenko et al. |
| 2007/0249254 A1 | 10/2007 | Mansfield |
| 2009/0163361 A1 | 6/2009 | Handlin, Jr. et al. |
| 2009/0258210 A1* | 10/2009 | Iyad et al. ..................... 428/220 |
| 2012/0123373 A1* | 5/2012 | Melik et al. ................... 604/369 |
| 2012/0207996 A1* | 8/2012 | Chapman et al. ............. 428/220 |

\* cited by examiner

TEAR RESISTANT FILM

FIELD OF THE INVENTION

The present invention is directed, generally, to a film that exhibits improved resistance to the undesired growth of a tear, hole, aperture or other discontinuity and a method for making such a film. Specifically, the present invention is directed to an elastomeric film material formed from an elastomeric polymer that exhibits suitable strain crystallization properties, especially at the leading tip of a tear or other discontinuity in the film, to help resist undesired growth of the tear or discontinuity.

BACKGROUND OF THE INVENTION

Elastic materials, especially elastic films, are commonly used for a wide variety of applications. For example, disposable absorbent articles typically include one or more components that rely on film materials, especially elastic film materials, to control the movement of liquids and to provide a comfortable, conforming fit when the article is worn by a wearer. However, conventional elastic film materials have been known to at least partially tear when subjected to the normal wear and tear on the article when in use. Such tearing may be related to, for example, material defects, contact with sharp objects, pulling and stretching by a wearer, rigorous activity of a wearer, and/or repetitive mechanical stress experienced during wear and/or manufacture. Additionally, it is not uncommon for film materials to be subjected to vigorous mechanical and/or thermal stress during various manufacturing processes (e.g., incremental stretching processes or bonding processes such as high pressure bonding, thermal bonding, and ultrasonic bonding), which may result in undesirable tears and/or holes in the film. In some instances, it may even be desirable to intentionally include one or more pre-formed discontinuities (e.g., one or more apertures) that extend at least partially through the thickness of the film, for example, to control the breathability, permeability to liquids and/or solids, opacity, and/or extensibility of the article or article component that includes the film.

Initially, openings in the film, whether desired or undesired, may start out small and be relatively inconsequential with regard to the desired function of the film, article component and/or article. But as the size of the opening grows, it may ultimately lead to partial or complete (catastrophic) failure of the film, article component and/or article. Unintended catastrophic failure of an article or article component is almost always undesirable, but when the article is a disposable absorbent article such as a diaper or training pant, the consequences of catastrophic failure of the article or component may be especially acute due to, for example, the possibility of bodily exudates escaping from the article and/or the article becoming separated from the wearer. To further compound the potential problems associated with conventional films, at least some manufacturers desire to use thinner and/or lower basis weight films to reduce material costs. The aforementioned problems associated with the formation of tears, holes, and apertures in a film may be even more acute in thinner/lower basis weight films.

In order to reduce the possibility that the elastic film incorporated into an article will fail due to the presence and/or formation of a hole, tear, and/or aperture, the strength of the film may be increased. Increasing the strength of the film typically means increasing the thickness of the film or forming the film from different materials, both of which may undesirably impact the cost and/or complexity of manufacturing the film or the suitability of the film for a particular use. For example, using a stronger film in an absorbent article such as a diaper or pant may result in an undesirable amount of pressure being applied to the skin of a wearer, which may lead to red-marking and/or discomfort. Additionally, increasing the overall strength of the film may only improve the film's resistance to the initial formation of a hole, tear, or aperture and not its subsequent growth.

Another method for reducing the possibility of undesired growth of a tear, hole, and/or aperture in a film, especially in a low basis weight film, includes joining one or more reinforcing layers to the film. For example, the film may be sandwiched between two or more nonwoven layers and/or the film may be formed with one or more commonly known "skin layers" (e.g., through a co-extrusion process). However, adding additional layers of material to improve the performance of the film may undesirably increase the cost and/or complexity of producing a particular article or article component that incorporates the film and/or make the film unsuitable for its intended purpose. Thus, there remains a need to provide a film suitable for use in an absorbent article that exhibits resistance to the growth of tears, holes, and/or apertures in a variety of circumstances (e.g., at a low basis weight) without the use of additional reinforcing materials.

Accordingly, it would be desirable to provide a film that has an improved resistance to the growth of a tear, hole, or aperture.

SUMMARY OF THE INVENTION

In order to provide a solution to the problems set forth above at least one embodiments describes an elastic film material that resists the propagation of a tear. The film material comprises an SEEPS elastomeric block copolymer and has a time to fail of at least 1 hour according to the Slow Tear Test. The film has a $T_m$, of between about 10° C. and 20° C.

DETAILED DESCRIPTION OF THE INVENTION

Definitions

Figure 1:
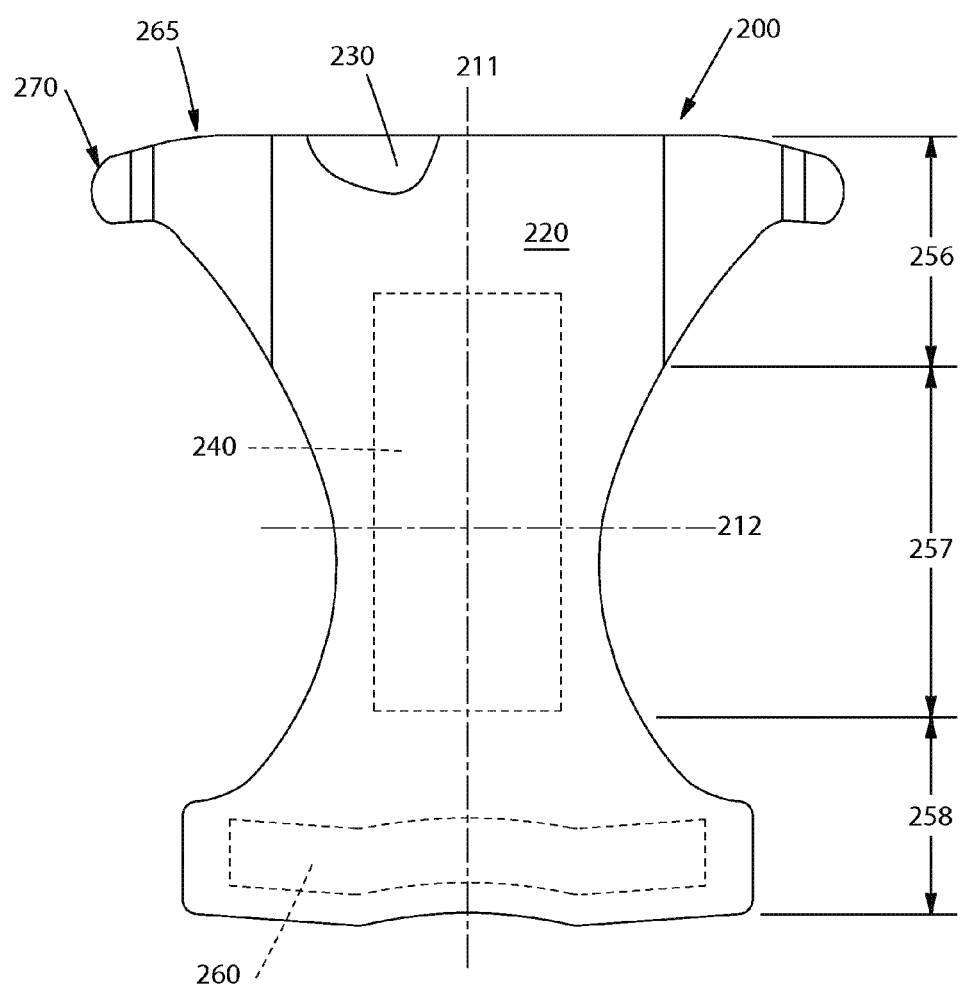
FIG. 1 is a plan view of an absorbent article.

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a preformed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Activation" is the mechanical deformation of a plastically extensible material that results in permanent elongation of the extensible material in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to a plastically extensible material typically results in permanent deformation of the plastic material, while the elastic material returns substantially to its original dimension. "Activate," and variations thereof, means subjecting a material to an activation process.

"Aperture" means an opening in a film purposefully added during filmmaking or laminate making, which is intended to impart a desired characteristic such as breathability. The growth of an aperture is the increase in the size of the aperture due to mechanical failure of the portion(s) of the film adjacent to the aperture.

"Basis weight" is the mass of a sheet or web of material divided by its surface area. The units for basis weight herein are grams per square meter (g/m$^2$).

"Breathable" means a film or laminate that give Air Permeability Values of between 5 and 50 m$^3$/m$^2$/min in the Air Permeability Test described below.

"Copolymer" means a polymer derived from two or more monomer species wherein the polymer chains each comprise repeat units from more than one monomer species.

"Crystalline melting temperatures" are determined by Differential Scanning calorimetry, which is described in more detail below. The melting endothermic peak temperature is taken as the $T_m$ ($T_{pm}$ per ASTM D3418-08) of a particular population of crystals. Materials of the current invention may have one or more melting endotherm peaks.

"Disposed" means an element is positioned in a particular place with regard to another element.

"Elastic," "elastomeric," and "elastically extensible" mean the ability of a material to stretch by at least 50% without rupture or breakage at a given load, and upon release of the load the elastic material or component exhibits at least 80% recovery (i.e., has less than 20% set). For example, an elastic material that has an initial length of 100 mm can stretch to at least 150 mm (50% stretch) and, upon removal of the force, retract to a length of 110 mm (i.e., have a set of 10 mm or 10%). Stretch, sometimes referred to as strain, engineering strain, percent strain, draw ratio or elongation, along with recovery and set may each be determined according to the Hysteresis Test described in more detail below. It is to be understood; however, that this definition of elastic does not apply to materials that do not have the proper dimensions (e.g., not wide enough) to be properly subjected to the Hysteresis Test. Instead, such material is considered to be elastic if it can stretch to at least 50% upon application of a biasing force, and return substantially to its original length (i.e., exhibit less than 20% set) upon release of the biasing force.

"Extensible" means the ability to stretch or elongate, without rupture or breakage, by at least 50%.

"Film" means a sheet-like material wherein the length and width of the material far exceed the thickness of the material (e.g., 10×, 50×, or even 1000× or more). Films are typically liquid impermeable but may be configured to be breathable.

"Hole" means an undesired opening in a film that can act as a "crack" in the Fracture Mechanics sense. The growth of a hole is the increase in the size of the hole due to mechanical failure of the portion(s) of the film adjacent to the hole.

"Joined" means configurations whereby an element is directly secured to another element by affixing the element directly to the other element, and configurations whereby an element is indirectly secured to another element by affixing the element to intermediate member(s) that in turn are affixed to the other element.

"Laminate" means two or more materials that are bonded to one another by any suitable method known in the art (e.g., adhesive bonding, thermal bonding, ultrasonic bonding, or high pressure bonding using non-heated or heated patterned roll).

"Longitudinal" means a direction running substantially perpendicular from a waist end edge to an opposing waist end edge of an absorbent article when the article is in a flat out, uncontracted state. "Lateral" refers to a direction running from a side edge to an opposing side edge of an article and generally perpendicular to the longitudinal direction.

"Machine direction" or "MD" is the direction parallel to the direction of travel of the web in a manufacturing process. The "cross machine direction" or "CD" is the direction substantially perpendicular to the MD and in the plane generally defined by the web.

"Nonwoven" means a porous, fibrous material made from continuous (long) filaments (fibers) and/or discontinuous (short) filaments (fibers) by processes such as, for example, spunbonding, meltblowing, airlaying, coforming, carding, hydroentangling, and the like. Nonwovens do not have a woven or knitted filament pattern. Nonwovens may be liquid permeable or impermeable.

"Plastic" and "plastically extensible" mean the ability of a material to stretch by at least 50% without rupture or breakage at a given load and, upon release of the load the material or component, exhibits at least 20% set (i.e., recovers less than 80%). For example, an extensible material that has an initial length of 100 mm can stretch at least to 150 mm (50% stretch) and, upon removal of the applied force, retract to a length of 135 mm (i.e., have a set of 35 mm (35% set), when subjected to the Hysteresis Test described below.

"Relaxed" means the state of an element, material or component at rest with substantially no external force acting on the element, other than gravity.

"Tear" means an undesired opening in a film that has intersected with one or more of the edges of the film, which can act as a "crack" in the Fracture Mechanics sense. The growth of a tear is the increase in the size of the tear due to mechanical failure of the portion(s) of the film adjacent to the tear.

"Web" means a material capable of being wound into a roll. Webs may be films, nonwovens, laminates, apertured films and/or laminates, and the like. The face of a web refers to one of its two dimensional surfaces, as opposed to its edge.

"X-Y plane" means the plane defined by the MD and CD of a moving web or the length and width of a piece of material.

Polymer

A number of elastomeric polymers can be used to make an elastic film. Nonlimiting examples of elastomeric polymers include homopolymers, block copolymers, random copolymers, alternating copolymers, graft copolymers, and the like. Particularly suitable polymers for use in films exhibiting resistance to tear propagation are block copolymers, which are typically made of blocks (or segments) of distinct repeat units that each contribute to the properties of the polymer.

One reason block copolymers are recognized as being useful, at least in part, is because the blocks of the copolymer are covalently bonded to one another and form microphase-separated structures with rubber domains that provide good extensibility while the glassy end block domains provide mechanical integrity (e.g., good mechanical strength and avoidance of unwanted stress relaxation or flow). Block copolymers suitable for use herein may exhibit both elastomeric and thermoplastic characteristics. For example, the end-blocks may form domains that display stiff, rigid mechanical properties at temperatures that prevail during end use (e.g., 20° C.-40° C.), thereby adding rigidity and strength to the entire polymer. Such an end-block is sometimes referred to as a "hard block". The midblock may accommodate the relatively large deformations associated with elastomers and provides retractive force when the material is strained (i.e., stretched or extended). Such a midblock is sometimes referred to as a "soft block" or "rubbery block." Suitable block copolymers for use herein include at least one hard block (A) and at least one soft block (B). The block copolymers may have multiple blocks. In certain embodiments, the block copolymer may be an A-B-A triblock copolymer, an A-B-A-B tetrablock copolymer, or an A-B-A-B-A pentablock copolymer. Other suitable copolymers include triblock copolymers having endblocks A and A', wherein A and A' are derived from different compounds. In certain embodiments, the block copolymers may having more than one hard block and/or more than one soft block, wherein each hard block may be derived from the same or different monomers and each soft block may be derived from the same or different monomers.

Suitable hard block components have a glass transition temperature ($T_g$) greater than 25° C. or 45° C. or even 65° C., but typically less than 100° C. The hard block portion may be derived from vinyl monomers including vinyl arenes such as styrene and alpha-methyl-styrene or combinations thereof. The soft block portion may be a polymer derived from conjugated aliphatic diene monomers. Typically, the soft block monomers contain fewer than 6 carbon atoms. Suitable diene monomers such as, for example, butadiene and isoprene may be used as-polymerized or in their hydrogenated form. Suitable soft block polymers include poly(butadiene), poly(isoprene), and copolymers of ethylene/propylene, ethylene/butene, and the like. In certain embodiments, it may be desirable to partially or fully hydrogenate any residual olefinic double bonds contained in the copolymer or portion thereof (e.g., midblock or endblock).

In a particularly suitable embodiment, the elastomeric polymer may be a styrene-ethylene-ethylene-propylene-styrene ("SEEPS") block copolymer that includes two polystyrene endblocks of approximately 8 kg/mole each and a 45 kg/mole midblock. The midblock may be formed, for example, by copolymerizing and then hydrogenating isoprene and butadiene. It may be desirable to hydrogenate the copolymer such that from 95-99% or even 98-99% of the original C=C double bonds in the midblock are saturated but the polystyrene endblocks remain aromatically intact. If the degree of hydrogenation is too low, the polymer may begin to lose its ability to undergo strain-induced crystallization. It is believed, without being limited by theory, that strain induced crystallization in a polymer is important for providing tear resistant characteristics to films made with such polymers. In certain embodiments, copolymerizing isoprene and butadiene to produce the rubbery midblock may result in a copolymer that varies both in comonomer sequence and in vinyl content. While a SEEPS copolymer is a block copolymer, the ethylene-ethylene-propylene ("EEP") midblock is more of a random copolymer than blocky or alternating. But subtle departures from randomness may occur. The departures from randomness, as well as the vinyl content of the copolymer, may be controlled by adjusting the conditions during polymerization. For example, copolymerization of isoprene and butadiene with subsequent hydrogenation may give rise to a variety of branch types. Table 1 below exemplifies the different branch types that may result. With the partial exception of the methyl branches, the branches typically do not "fit" into the polyethylene-type crystals, and therefore decrease the midblock's degree of crystallinity and $T_m$. For example, the midblock of a SEEPS block copolymer may be approximately 7% crystalline at temperatures below −50° C. and have a $T_m$ of approximately 0° C. In comparison, a substantially unbranched polyethylene is approximately 75% crystalline and has a $T_m$ of approximately 135° C.

TABLE 1

| Isomer | Branch Type After Hydrogenation |
|---|---|
| 1,2 Isoprene | Methyl, Ethyl |
| 3,4 Isoprene | Isopropyl |
| 1,4 Isoprene | Methyl |
| 1,2 Butadiene | Ethyl |
| 1,4 Butadiene | No branch - possible to crystallize |

The length of the runs of crysallizable $CH_2$ sequences, which directly impact the melting temperature of the polymer midblock, depends, at least partially, on the sequence of comonomer incorporation into the midblock (e.g., isoprene always gives a branch of some type) and the overall balance between 1,4 and 1,2 (or 3,4) polymerization of the dienes. The $T_m$ of the crystal may provide information about the length of the crystallizable sequences and the ability of the material to undergo strain-induced crystallization, both of which are related to the number, type, and distribution of the branches on the midblock backbone. Suitable elastomers herein include sufficiently long crystallizable sequences of $CH_2$ groups (which form polyethylene-type crystals) that have a $T_m$ of greater than 10° C. (compared to, e.g., −5° C. for previously known materials). A suitable $T_m$ for the elastomers herein is between 10° C. and 20° C., 12° C. and 18° C.; 13° C. and 17° C.; or even between 14° C. and 16° C.

In addition to the EEP midblocks described above, it may be desirable to provide a midblock of the "EB" type (i.e., hydrogenated polybutadiene) that contains similar crystallizable sequences, for example, by choosing the appropriate solvent polarity (which controls 1-4 vs. 1-2 content), as described in *Anionic Polymerization: Principles and Practical Applications*, Henry Hsieh, Roderick Quirk; Chapter 9, pp. 197-229; Marcel Decker, New York (1996).

Film

Unlike conventional elastomeric films (e.g., films formed from known elastomers such as Vector 4211 from Dexco Polymers L.P., Houston, Tex.), which form films that exhibit minimal or no tear resistance, the elastic films disclosed herein include an effective amount of at least one elastic polymer that imparts suitable tear resistance to the film. It is to be appreciated that such resistance is not limited to tears, but also includes slits, apertures, openings, holes, and/or any other discontinuities in the film. The Slow Tear Test, described in more detail below, provides a suitable method for quantifying a film's resistance to the growth of a tear, hole, aperture, or other discontinuity. Suitable time-to-fail values for films disclosed herein include values of greater than 1 hour, 2 hours, 4 hours, 6 hours, 10 hours, 15 hours, or even up to 24 hours or more, for example up to 30 hours, 36 hours, 40 hours, 44 hours, 48 hours, or even up to 60 hours when measured according to the Slow Tear Test. Ideally, the film is capable of resisting the growth of a tear indefinitely. While the present films desirably provide suitable resistance to the growth of a tear as described herein, it may also be desirable for the films herein to exhibit resistance to the rapid application of a relatively high amount of mechanical stress. For example, the present films may have a High-Speed Tensile Strength of between 10 and 25 MPa; 15 and 20 MPa; 16 and 19 MPa; or even between 17 and 18 MPa when measure according to the High Speed Tensile Test described in more detail below. It may also be desirable to provide a film that exhibits a Notched High Speed Tensile Strength of between 10 and about 20; MPa; 14 and 19 MPa; or even between 15 and 18 MPa when measure according to the Notched High-Speed Tensile Strength Test described in more detail below. It is believed, without being limited by theory, that suitable High Speed Tensile and/or Notched Tensile Strengths in a film may be important for providing at least some resistance to film failure related to relatively high rates of undesired mechanical stress.

The present tear resistant films are not limited to any particular dimension, and may be configured as relatively thin sheets of material. In certain embodiments, the film may have an Effective Average Thickness, of between 1 µm-1 mm; 3 µm-500 µm; or 5 µm-100 µm, or any value in these ranges. Suitable basis weight ranges for the films disclosed herein include from 20 to 140 $g/m^2$, for example from 25 to 100 $g/m^2$; from 30 to 70 $g/m^2$; or even from 35 to 45 $g/m^2$. The tear resistant films may be formed by any suitable method in the art such as, for example, extruding a molten thermoplastic and/or elastomeric polymer through a slit die and subsequently cooling the extruded sheet. Other non-limiting examples for making films include casting, blowing, solution casting, calendering, and formation from aqueous or cast, non-aqueous dispersions. Suitable methods of producing films from polymeric materials are described in *Plastics Engineering Handbook of the Society of the Plastics Industry, Inc.*, Fourth Edition, 1976, pages 156, 174, 180 and 183. In certain embodiments, the elastic film may have a loading engineering stress at 200% strain (L200) of between about 0.8 and 2 MPa, 1.0 and 1.5 MPa, or even between 1.0 and 1.2 MPa, and an unloading engineering stress at 50% strain (UL50) of between 0.3 and 0.8, 0.4 and 0.6, or even between 0.5 and 0.6 MPa according to the Hysteresis Test described in more detail below. The L200 and UL50 values disclosed above may be important for providing a film that is suitable for use in a disposable absorbent article (e.g., for providing low force recovery stretch, a snug comfortable fit, less undesired sag, containment of bodily exudates in a desired location, strength to resist the initial formation of a hole or tear).

The present tear resistant films may include one or more additives commonly used in the art to tailor a film for a particular use. For example, stabilizers, antioxidants, and bacteriostats may be employed to prevent thermal, oxidative, and bio-chemical degradation of the film or film component. In certain embodiments, it may be desirable to include a modifying resin in the film composition to provide desirable elastic recovery characteristics, for example, as disclosed in U.S. Pat. No. 7,717,893 to Hird, et al. Generally, the additive or additives may account for 0.01% to 60%; 0.01% to 25%; or even 0.01% to 10% of the total weight of the film.

Suitable examples of stabilizers and antioxidants are well known in the art and include high molecular weight hindered phenols (i.e., phenolic compounds with sterically bulky radicals in proximity to the hydroxyl group), multifunctional phenols (i.e., phenolic compounds with sulfur and phosphorous containing groups), phosphates such as tris-(p-nonylphenyl)-phosphite, hindered amines, and combinations thereof. Representative hindered phenols include t-butylhydroxyquinone; 1,3,5-trimethyl-2,4,6-tris(3-5-di-tert-butyl-4-hydroxybenzyl)benzene; pentaerythritol tetrakis-3(3,5-di-tert-butyl-4-hydroxyphenyl)propionate; n-octadecyl-3(3,5-ditert-butyl-4-hydroxyphenyl)propionate; 4,4'-methylenebis (4-methyl-6-tert butylphenol); 4,4'-thiobis(6-tert-butyl-o-cresol); 2,6-di-tert-butylphenol; 6-(4-hydroxyphenoxy)-2,4-bis(n-ocytlthio)-1,3,5-triazine; 2,4,6-tris(4-hydroxy-3,5-di-tert-butyl-phenoxy)-1,3,5-triazine; di-n-octadecyl-3,5-di-tert-butyl-4-ydroxybenzylphosphonate; 2-(n-octylthio) ethyl-3,5-di-tert-butyl-4-hydroxybenzoate; and sorbitol hexa-(3,3,5-di-tert-butyl-4-hydroxy-phenyl) propionate. Proprietary commercial stabilizers and/or antioxidants are available under a number of trade names including a variety of Wingstay®, Tinuvin® and Irganox® products.

Examples of suitable bacteriostats include benzoates, phenols, aldehydes, halogen containing compounds, nitrogen compounds, and metal-containing compounds such as mercurials, zinc compounds and tin compounds. A representative bacteriostat is 2,4,4'-trichloro-2'-hydroxy-diphenyl-ether which is available under the trade designation IRGASAN PA from Ciba Specialty Chemical Corporation, Tarrytown, N.Y.

Other optional additives include thermoplastic polymers or thermoplastic polymer compositions which preferentially associate with the hard blocks or segments of the block copolymers. Without intending to be bound by theory, it is believed that these thermoplastic polymers become incorporated into the entangled three-dimensional network structure of the hard phase. This entangled network structure can provide improved tensile, elastic and stress relaxation properties of the elastomeric composition. Where the elastomeric polymer comprises a styrenic block copolymer, thermoplastic polymer additives such as polyphenylene oxide and vinylarene polymers derived from monomers including styrene, alpha-methyl styrene, para-methyl styrene, other alkyl styrene derivatives, vinyl toluene, and mixtures thereof, are useful herein because they are generally considered to be chemically compatible with the styrenic hard blocks of the block copolymer.

Various viscosity modifiers, processing aids, slip agents or anti-block agents can be employed as additives to provide improved handling characteristics or surface characteristics. Processing aids include processing oils, which are well known in the art and include synthetic and natural oils, naphthenic oils, paraffinic oils, olefin oligomers and low molecular weight polymers, vegetable oils, animal oils, and derivatives of such including hydrogenated versions. Processing oils also may incorporate combinations of such oils. A particularly suitable processing oil is mineral oil. Viscosity modifiers are also well known in the art. For example, petroleum derived waxes can be used to reduce the viscosity of the elastomeric polymer in thermal processing. Suitable waxes include low number-average molecular weight (e.g., 600-6000) polyethylene; petroleum waxes such as paraffin wax and microcrystalline wax; atactic polypropylene; synthetic waxes made by polymerizing carbon monoxide and hydrogen such as Fischer-Tropsch wax; and polyolefin waxes.

Various colorants and fillers are known in the art and may be included as additives in the film composition. Colorants can include dyes and pigments such as titanium dioxide. Fillers may include such materials as talc and clay. Other additives may include dyes, UV absorbers, odor control agents, perfumes, fillers, dessicants, and the like.

In certain embodiments, it may be desirable to provide pre-formed apertures (i.e., apertures that are intentionally provided in the film during a manufacturing process) that extend through the thickness of the film. The apertures may have any suitable size and/or shape desired. For example, the apertured film may have circle-shaped, individual apertures with a diameter of between 0.2 and 3 mm and an open area of 5-60% (e.g., 10-30% or 15-25%). In another example, the apertured film may include slits that can "opened up" by applying a transverse force to form round, rectangular, diamond-shaped apertures, combinations of these, and/or any other suitable shape desired with a largest dimension in the x-y plane of the film of between 0.2 and 3 mm. In still another example, the apertures may extend three-dimensionally through the film and form a cone-like structure. In such an example, the tapered, cone-like structure may include a first opening having a first diameter in the plane of the film (major diameter) and a second opening having a second, smaller diameter at the opposing end of the cone (minor diameter). Aperture size and open area are measured according to the method set forth in U.S. Publication No. 2007/0073256 filed by Ponomorenko, et al., on Sep. 22, 2006 and titled "Absorbent Article With Sublayer." Suitable methods for forming apertures in a film are commonly known in the art and include, for example, die punching, slitting, hot-pin melt aperturing, vacuum forming, high pressure jet aperturing, embossing rolls, combinations of these and the like. In conventional films, aperture pattern selection may be largely dictated by the need to minimize stress concentration around the apertures, thereby mitigating the risk of tearing the film during mechanical activation. But the film disclosed herein is not so limited, and therefore may provide improved manufacturing flexibility when selecting an aperture pattern and/or size. Suitable examples of apertured films and methods of aperturing films are disclosed in U.S. Pat. No. 6,410,129 issued to Zhang, et al., on Jun. 25, 2002 and titled "Low Stress Relaxation Elastomeric Materials;" U.S. Pat. No. 7,307,031 issued to Carroll, et al., on Dec. 11, 2007 and titled "Breathable composite sheet structure and absorbent articles utilizing same;" U.S. Pat. No. 4,151,240, issued to Lucas et al., on Apr. 24, 1979 and titled "Method for Debossing And Perforating A Running Ribbon Of Thermoplastic Film;" U.S. Pat. No. 4,552,709 issued to Koger, II, et al., on Nov. 12, 1985 and titled "Process For High-Speed Production Of Webs Of Debossed And Perforated Thermoplastic Film;" U.S. Pat. No. 3,929,135, to Thompson, issued on Dec. 30, 1975 and titled "Absorptive Structures Having Tapered Capillaries;" U.S. Pat. No. 4,324,246 issued to Mullane, et al. on Apr. 13, 1982 and titled "Disposable Absorbent Article Having A Stain Resistant Topsheet;" U.S. Pat. No. 4,342,314, issued to Radel, et al., on Aug. 3, 1982 and titled "Resilient Plastic Web Exhibiting Fiber-Like Properties;" U.S. Pat. No. 4,463,045 issued to Ahr, et al., on Jul. 31, 1984 and titled "Macroscopically Expanded Three-Dimensional Plastic Web Exhibiting Non-Glossy Visible Surface and Cloth-Like Tactile Impression;" and U.S. Pat. No. 4,591,523 issued to Thompson on May 27, 1986 and titled "Apertured Macroscopically Expanded Three-Dimensional Polymeric Web Exhibiting Breatheability And Resistance To Fluid Transmission."

In certain embodiments, it may be desirable to incorporate the film into a laminate such as, for example, a tri-laminate structure with one or more film layers sandwiched between two or more nonwoven layers (e.g., a film layer sandwiched between two SMS nonwoven layers). Suitable examples of laminate structures are disclosed in co-pending U.S. Ser. No. 13/026,548, filed on Feb. 14, 2011 by Mansfield, titled "Tear Resistant Laminate" and U.S. Publication No. 2007/0249254 filed by Mansfield on Apr. 24, 2006 and titled "Stretch Laminate, Method of Making and Absorbent Article".

In certain embodiments, the film and/or film containing laminate may be incorporated into an article (e.g., a diaper or training pant), where it is particularly important that the article function as intended for a predetermined amount of time. Thus, suitable time-to-fail values are important for providing an indication that an article or article component that includes the film is less likely to suffer catastrophic failure in use.

FIG. 1 shows an exemplary embodiment of a diaper 200 in a flat-out, uncontracted state (i.e., with no elastic induced contraction). Portions of FIG. 1 are cut away to more clearly show the construction of the diaper 200. The outer, garment-facing surface of the diaper 200 is oriented towards the viewer and the opposing inner, wearer-facing surface is oriented away from the viewer. The diaper 200 as shown in FIG. 1 has a longitudinal centerline 211 extending in the longitudinal direction and a lateral centerline 212 orthogonal thereto. The diaper 200 may include a first waist region 256, a second waist region 258, and a crotch region 257 disposed therebetween. As shown in FIG. 1, the diaper 200 may include a liquid pervious topsheet 230; a liquid impervious outer cover 220 joined with at least a portion of the topsheet 230, for example, along the periphery of the diaper 200; and an absorbent core assembly 240 positioned between the topsheet 230 and the outer cover 220. The inner, wearer-facing surface of the diaper 200 may include at least a portion of the topsheet 30 and other components, which may be joined to the topsheet 30. The outer, garment-facing surface may include at least a portion of the outer cover 220 and other components, which may be joined to the outer cover 220. The diaper 200 may include an elastic waist feature 260 and a fastening system. The fastening system may include an ear 265 joined to at least one of the front and back waist regions 256 and 258 and extending laterally outward therefrom. In certain embodiments, the ear 265 and one or both waist regions 256 and/or 258 may be formed from as a unitary structure, for example, by forming the two elements from the same substrate. The ear 265 may include a fastening tab 270, which extends laterally outwardly therefrom. The fastening tab 270 may include a fastening element that is engageable with another portion of the diaper 200. "Engageable" means one element is configured to be joined to another element, for example, through the creation of an entanglement-type mechanical bond. Nonlimiting examples of suitable absorbent articles for use with the tear resistant film disclosed herein may be found in U.S. Pat. Nos. 3,860,003; 4,808,178; 4,909,803; 5,151,092; 5,221,274; 5,554,145; 5,569,234; 5,580,411; 6,004,306; 7,626,073; U.S. Publication No. 2007/0249254; and copending U.S. Ser. No. 13/026,563, titled "Absorbent Article With Tear Resistant Components, filed on Feb. 14, 2011 by Mansfield.

Test Methods.

Environmental conditions for the test methods herein include a temperature of 23° C.±2° C., unless indicated otherwise. In some instances, the sample to be tested may include one or more layers of material in addition to the film material (e.g., samples taken from commercially available articles). In such instances, the film is carefully separated from the other layers of material so that damage to the film is avoided. If the film is damaged (i.e., torn, cut, punctured, etc.) as a result of separating the film from the other material, discard the sample and obtain another that is undamaged.

Hysteresis

Figure 10:
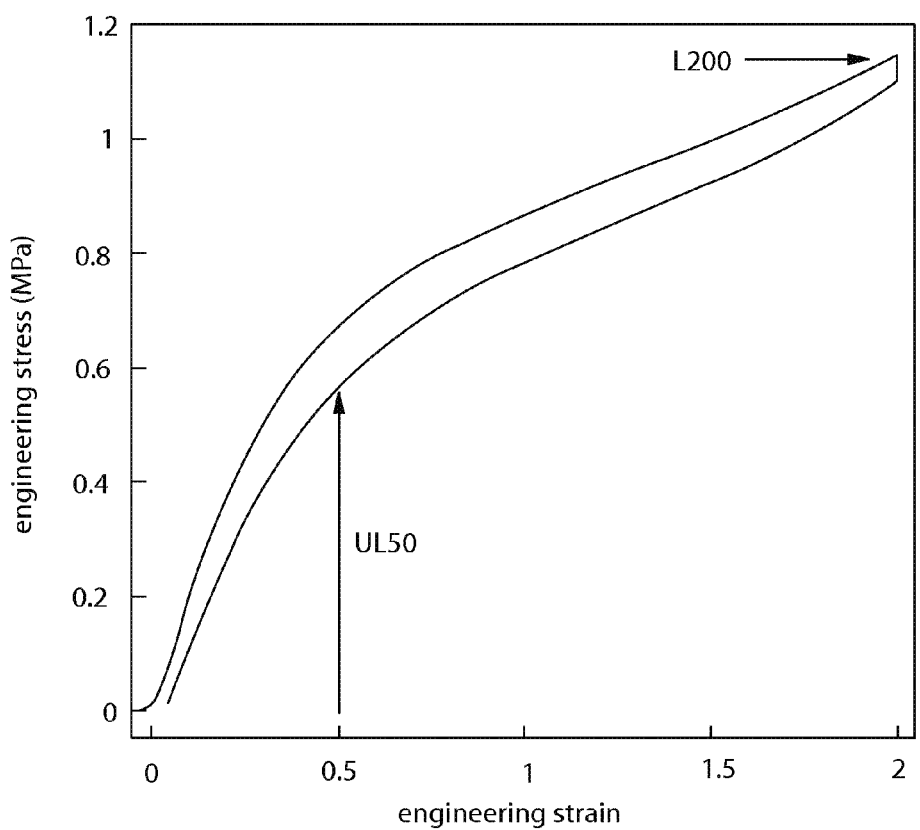
FIG. 10 is a chart illustrating an exemplary stress-strain curve generated during the Hysteresis Test.

The Hysteresis test is performed in accordance with ASTM D882-02 using line-contact grips and a load-hold-unload sequence, along with the exceptions and/or conditions set forth below. FIG. 10 is provided to illustrate the portion of the stress-strain curve that includes the L200 value (i.e., the engineering stress at 200% strain during loading) and the UL50 value (i.e., the engineering stress at 50% strain during unloading) generated during the Hysteresis test. One load-unload cycle is run.

specimen width: 25.4 mm
gauge length: 25.4 mm
testing speed: 4.233 mm/s
temperature: 22-24 C
applied displacement: 50.8 mm (200% engineering strain)
hold time at the applied displacement: 30 seconds
If grip design does not accommodate the 50 mm extra sample length indicated in section 6.1 of ASTM D882-02, prepare samples to a length that allows gripping the appropriate gauge length without interfering with other parts of the grip. In such cases care must be taken to mount the specimen with proper alignment, gripping and gauge definition.

Record the following:
engineering stress at 200% engineering strain during the load segment (L200)
engineering stress at 50% engineering strain during the load segment (UL50)
engineering strain during unloading where the sample goes slack (Ls).

The set is then defined as Ls, expressed as a proportion of the engineering strain at applied displacement. For example if 200% engineering strain is applied to the sample and it goes slack at an engineering strain of 20% during unloading, the set is calculated as 20%/200%=0.10=10%.

When using the hysteresis test to determine whether a material meets the definition of "elastic" or "plastic" as described in the definitions, an applied displacement of 12.7 mm (i.e. an engineering strain of 50%) is used.

Basis Weight (Mass Per Unit Area)

The basis weight of each film is determined according to INDA Standard Test WSP 130.1 (09). All conditioning and testing is conducted in an atmosphere of 23±2° C., and 50±5% relative humidity.

The average of 5 specimens is reported as the Average Basis Weight in grams per square meter (gsm) to 3 significant digits.

Effective Average Thickness

The Effective Average Thickness of the film is calculated from the Average Basis Weight as follows.

Effective Average Thickness=Average Basis Weight/density

Units:
Thickness: micrometers (μm)
Basis Weight: gsm
density=0.92 grams per cm$^3$ (g/cc)
Results are reported in microns (μm) to 3 significant digits.

Air Permeability Test

The air permeability of a substrate (e.g., film, laminate, or article component) is determined by measuring the flow rate of standard conditioned air through a test specimen driven by a specified pressure drop. This test is particularly suited to materials having relatively high permeability to gases, such as nonwovens, apertured films and the like. ASTM D737 is used, modified as follows.

A TexTest FX3300 instrument or equivalent is used, which are available from Textest AG, Switzerland, or from Advanced Testing Instruments ATI in Spartanburg S.C., USA. The procedures described in the Operating Instructions for the TEXTEST FX 3300 Air Permeability Tester manual for the Air Tightness Test and the Function and Calibration Check are followed. If a different instrument is used, similar provisions for air tightness and calibration are made according to the manufacturer's instructions.

The test pressure drop is set to 125 Pascal and the 5 cm$^2$ area test head (model FX3300-5) is used. After making the measurement of a specimen according to the procedure given in the Operating Instructions for the TEXTEST FX 3300 Air Permeability Tester manual, the result is recorded to three significant digits. The average of 5 specimens air permeability data of this sample (in m$^3$/m$^2$/min) is calculated and reported as the Air Permeability Value.

Differential Scanning calorimetry (DSC).

Figure 2:
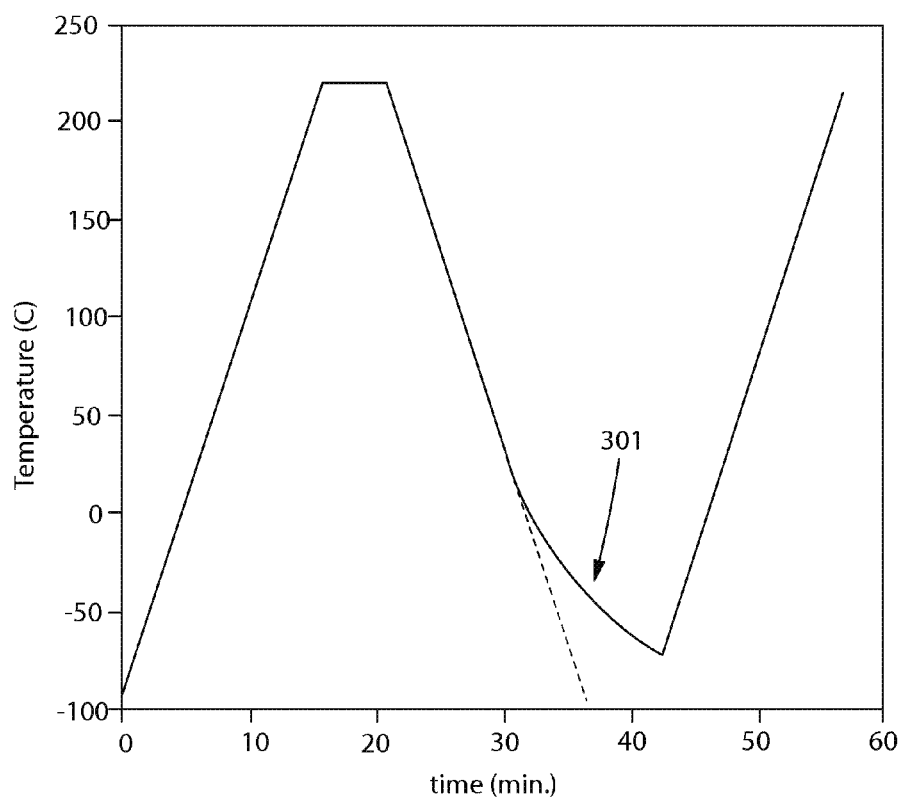
FIG. 2 is a chart of time versus temperature for use with the DSC test.

The DSC test is used to measure the melting temperature ($T_m$) of a polymer. The $T_m$ is determined by DSC measurements according to ASTM D3418-08 (note that $T_m$ is referred to as $T_{pm}$ in the ASTM method), except that the time-temperature profile shown in FIG. 2 is used for the measurement. Calibration is performed with a heating rate of 20° C./min. The temperature profile may include the non-linear portion 301 of profile at Time=30-42 minutes, as shown in FIG. 2. The non-linear portion 301 is a manifestation of limitations in the cooling capability of the apparatus. It is recognized that this deviation from the nominal cooling rate might have a modest effect on the observed melting curve, but all DSC data herein follow the same profile.

Slow Tear Test (time-to-fail).

The purpose of the Slow Tear Test is to measure the time-to-fail for a notched film sample. It is believed that the Slow Tear Test provides an indication of how well a film with tears, holes, or other defects resists propagation of the tear, hole, or defect, and in particular measures the time-to-fail for a notched film sample held at 37.8° C. and an engineering strain of 150%.

Figure 3:
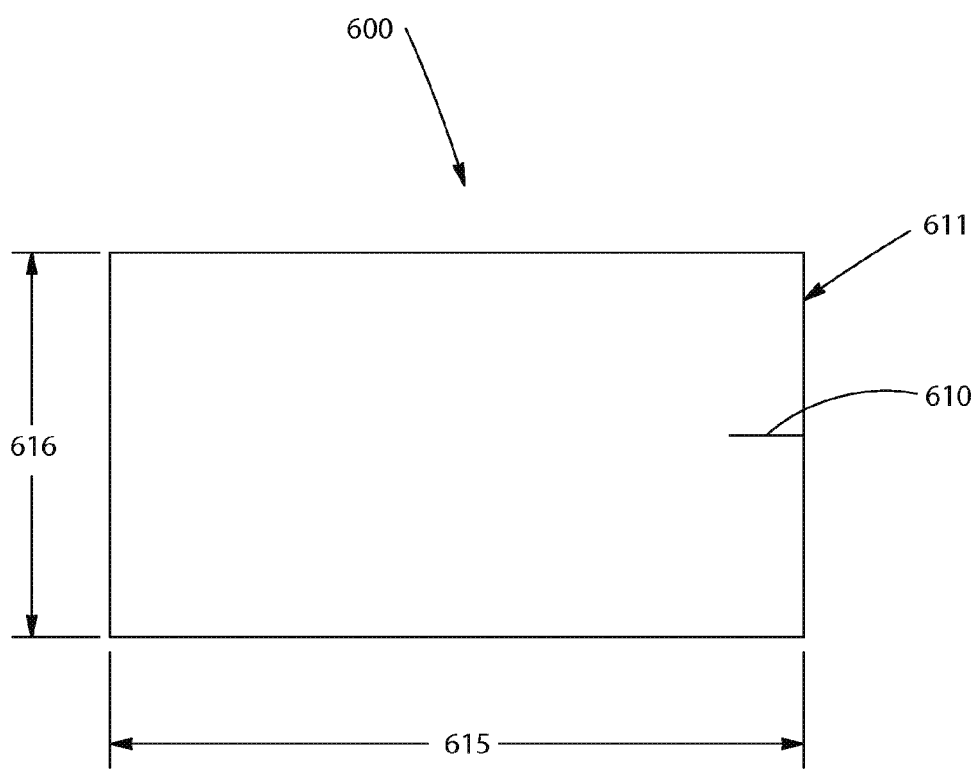
FIG. 3 is a side view of grip suitable for use with the Slow Tear Test.
Figure 5:
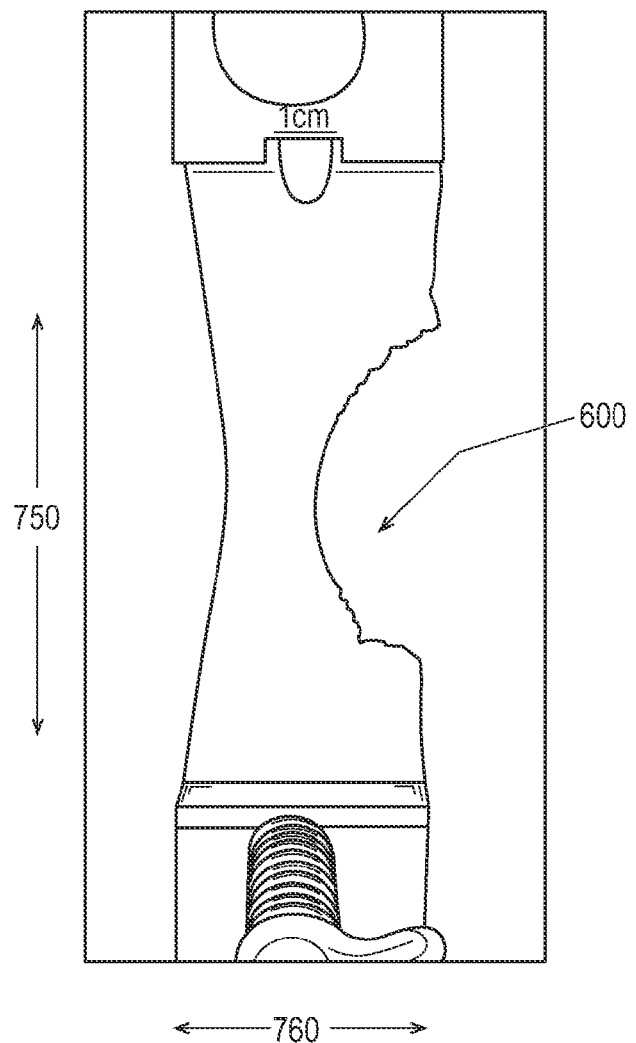
FIG. 5 shows a sample being subjected to the Slow Tear Test.

Setup
Gauge Length: 25.4 mm
Sample Width: 25.4 mm
Notch Length: 2 mm (single edge notch)
Testing Temperature: 37.8° C.
Applied engineering strain: 150% (i.e. apply and hold 38.1 mm of displacement.)
Direction of applied deformation: the same direction that the film would be strained during normal use of the article Sample Preparation FIG. 3 is provided to illustrate particular aspects of the sample preparation. On a cutting mat, the film material is sandwiched between sheets of photocopier paper. The top sheet of paper has lines printed on it to facilitate cutting the sample 600 to the correct dimensions and for correct notch 610 length. A sharp, X-ACTO brand knife and straight edge are used to prepare the samples 600. A sample 600 is cut such that it has a width 615 of 25.4 mm and a length 616 that is suitable for loading the sample into the grips and is sufficient to provide a gauge length of 25.4 mm without undesirably interfering with the test. Cut a 2 mm notch 610 extending inward from the side edge 611 of the sample 600 and perpendicular thereto. In this particular example, the width 615 and length 616 of the sample 600 coincide with the machine direction 750 and transverse direction 760, respectively, as shown in FIG. 5, such that the direction in which the sample is deformed is the transverse direction 760 during testing.

Grips

Figure 4:
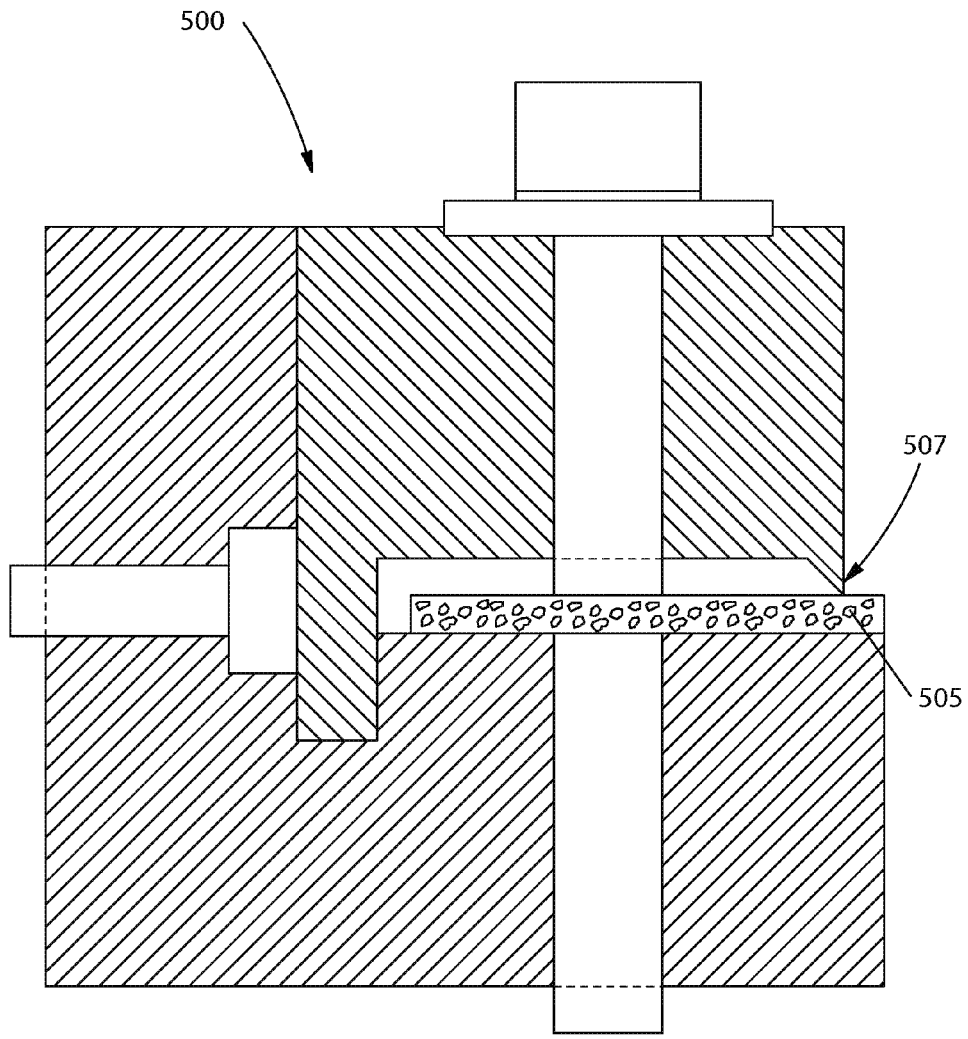
FIG. 4 is a plan view of notched sample for use in the Slow Tear Test.
Figure 6:
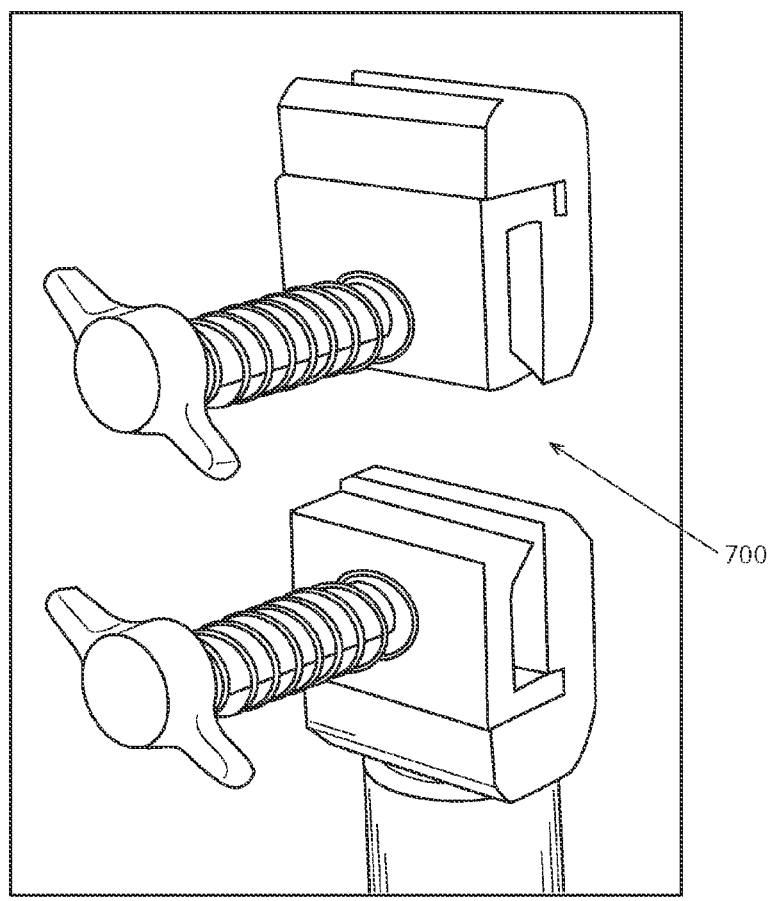
FIG. 6 shows a pair of opposing grips for use in the Slow Tear Test.

Line contact grips 500 of the type shown in FIG. 4 are used for this test. The line grips 500 are selected to provide a well-defined gauge and avoid undue slippage. The sample is positioned such that it has minimal slack and the notch is centered between the grips. The apexes 507 of the grips 500 are ground to give good gauge definition while avoiding damage or cutting of the sample. The apexes are ground to provide a radius in the range of 0.5-1.0 mm. A portion of one or both grips 500 may be configured to include a material 507 that reduces the tendency of a sample to slip, (e.g., a piece of urethane or neoprene rubber having a Shore A hardness of between 50 and 70). FIG. 6 shows a pair of opposing grips 700 suitable for use herein.

Apparatus

The grips are mounted in a frame (e.g., Chatillon MT 150L or similar) that allows hand-operated movement of one grip with respect to the other. Gauge blocks are used to establish precise grip positions for sample loading and sample testing. The entire frame is mounted in a chamber equipped with temperature control equipment well suited for maintaining the air temperature in the immediate proximity of the sample at 37.8° C.

Figure 7:
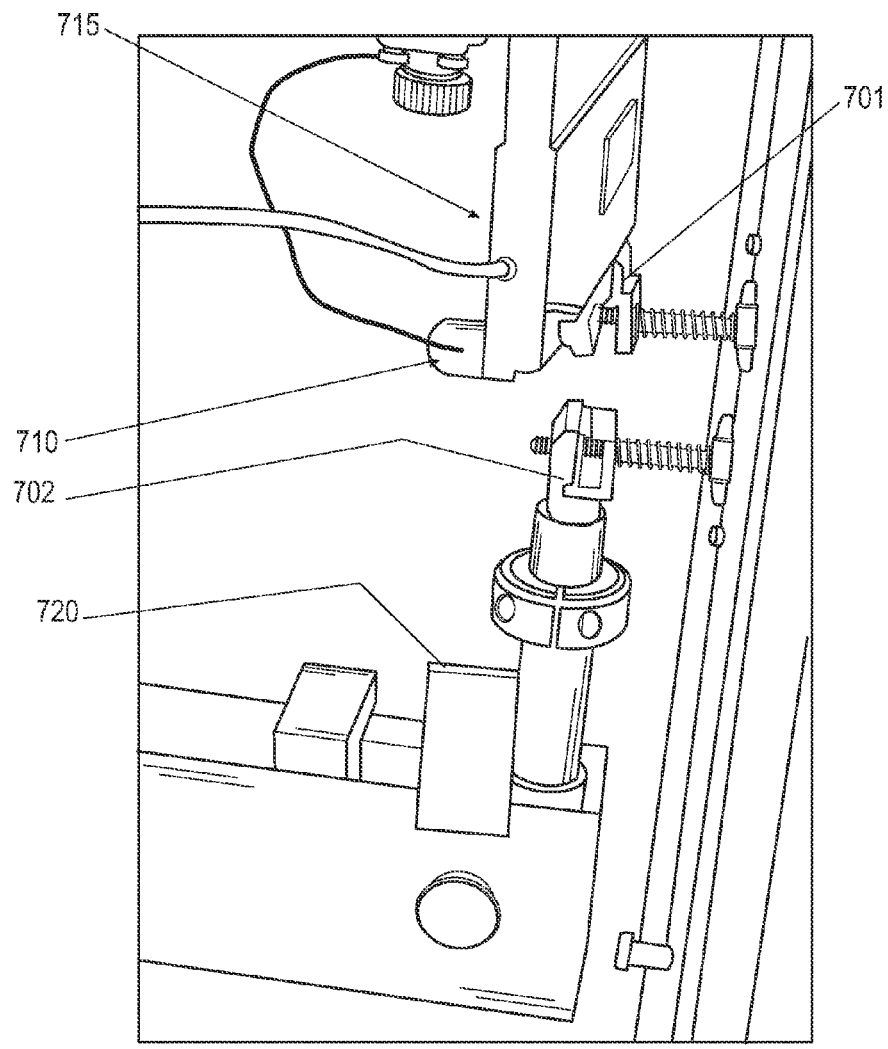
FIG. 7 shows an apparatus and set up for the Slow Tear Test.

FIG. 7 shows an exemplary apparatus 800 for conducting the Slow Tear Test. As shown in FIG. 7, the apparatus 800 is set up in a temperature control chamber and includes a top grip 701, a bottom grip 702, a gauge block 720 for precisely positioning at least the bottom grip 702, and a thermocouple 710 for monitoring the temperature in the chamber. A force transducer 715 is deployed in mechanical communication with the top grip 701. The force transducer 715 includes a suitable quality signal conditioner for enabling the desired force measurement without significant drift, noise, etc. The force transducer is selected to provide adequate resolution to identify when the final failure of a sample occurs. The output from the signal conditioner is connected to an analog-to-digital converter interfaced with a computer to allow data acquisition during the test. The force data are sampled at a frequency of at least one data point per second while the sample is being extended and during its initial force decay. The frequency of subsequent data sampling must be sufficient to determine the time-to-fail of a sample from the data to within 5% of the actual time-to-fail value of the sample. Time=0 is assigned to the first data point after the sample is extended 150% (i.e., 1 second after extension is complete).

Testing

Figure 8:
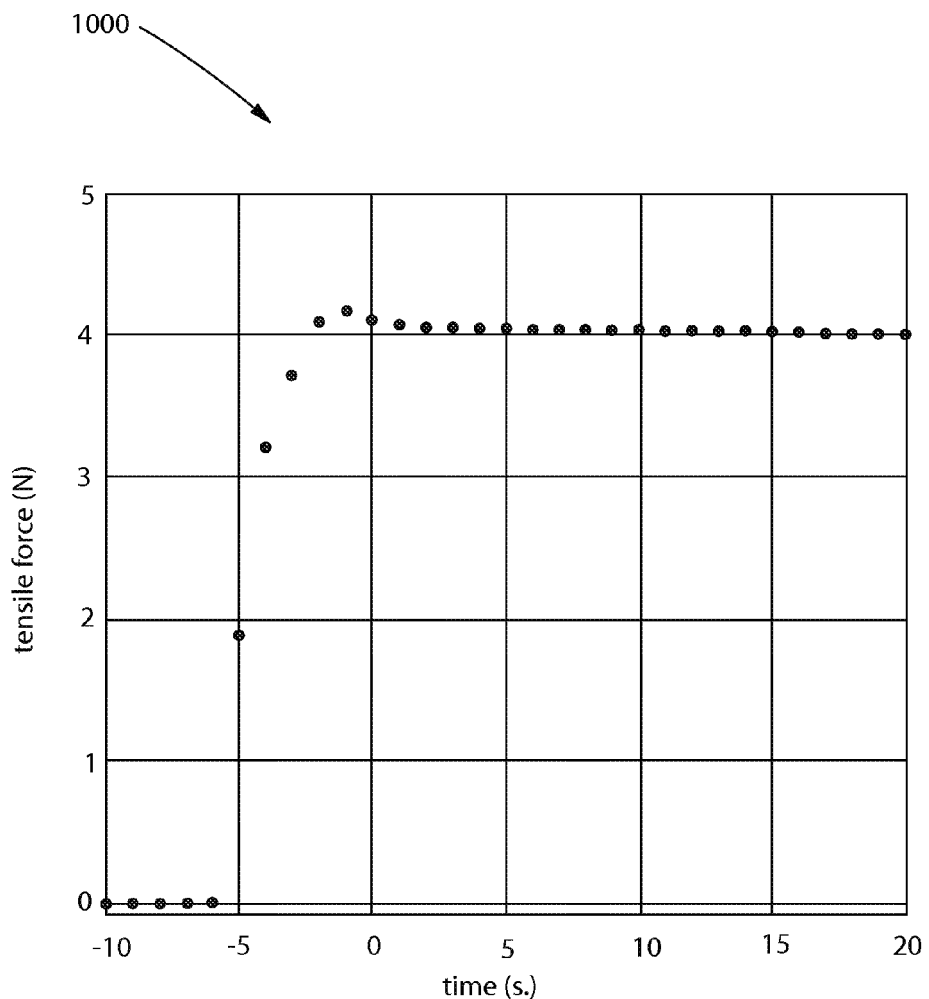
FIG. 8 is a chart of tensile force versus time for the Slow Tear Test.

The grip separation (i.e., gauge length) is set at 25.4 mm and the sample is inserted so that the grips form well-defined lines of contact on the sample. If surface tackiness makes it difficult to mount the sample then a powder such as corn starch may be used to mitigate tack. The grip bolts are tightened to provide a secure grip, but without cutting the sample. The temperature chamber door is closed to allow the temperature to equilibrate at target temperature for two minutes. Data acquisition is commenced. The desired displacement (38.1 mm) is applied to the sample over the course of 5 seconds as shown in FIG. 8 (i.e., from Time=−6 to Time=−1). FIG. 8 shows a chart 1000 illustrating the time versus force data that are collected during the test at one-second intervals. As used herein, "time-to-fail" means the time at which the sample breaks and the force reaches its unloaded baseline value.

High Speed Tensile Test

The High Speed Tensile Test is used to measure the Tensile Strength of a sample at a relatively high strain rate. The method uses a suitable tensile tester such as an MTS 810, available from MTS Systems Corp., Eden Prairie Minn., or equivalent, equipped with a servo-hydraulic actuator capable of speeds exceeding 5 m/s after 28 mm of travel, and approaching 6 m/s after 40 mm of travel. The tensile tester is fitted with a 50 lb. force transducer (e.g., available from Kistler North America, Amherst, N.Y. as product code 9712 B50 (50 lb)), and a signal conditioner with a dual mode amplifier (e.g., available from Kistler North America as product code 5010). Suitable grips such as those described above may be used to secure the samples during tensile testing.

Film samples having dimensions of 19 mm wide×16.5 mm long are prepared in the same manner described above for the Slow Tear Test. The mass of each sample measured is to within ±0.1 mg, and the length of each sample is measured to within ±0.1 mm. The tensile grips are moved to a grip separation of 10 millimeters (i.e. the distance between the lines of contact between sample and grip surface). The sample is mounted in the grips, optionally using powder such as corn starch (to kill the sample's tack, after sample has been weighed) and a thin piece of tape to help hold the sample straight and flat while mounting in grips (if used, tape must remain behind the lines of gripping so that it does not interfere with the sample's gauge during the test). The grips are moved close together to put as much slack as possible into the film sample without the grips interfering with one another. Actuator movement is selected such that the sample sees a grip speed of between 5 and 6 meters per second at break. Typically, during testing, one of the grips is kept stationary and the opposing grip is moved, but embodiments wherein both grips move are also contemplated herein.

Figure 9:
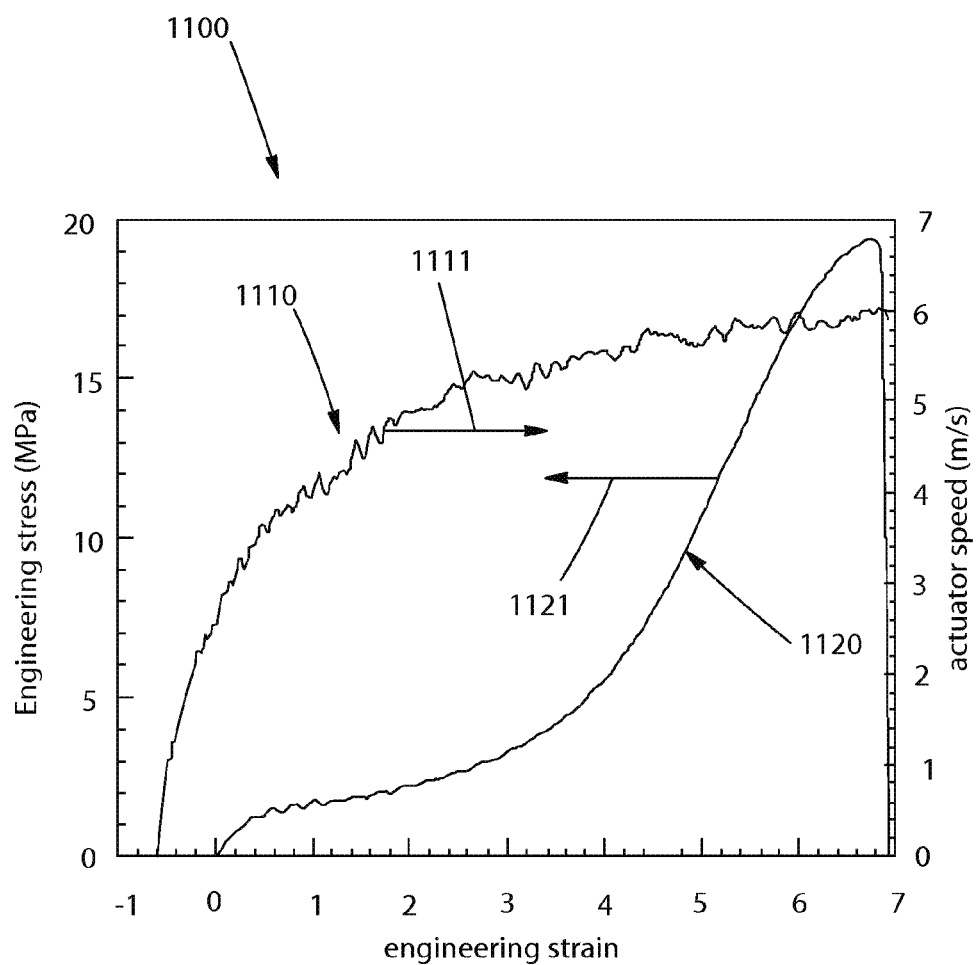
FIG. 9 is a chart of a suitable deformation regimen for the High Speed Tensile Test.

FIG. 9 illustrates a suitable, exemplary deformation regimen depicted as a chart 1100 with two curves 1110 and 1120. The first curve 1110 illustrates a plot of actuator speed (i.e., the relative speed at which one grip is moving away from the other grip) versus engineering strain. The arrow 1111 points to the y-axis used for this plot 1110. The second curve 1120 illustrates a plot of engineering stress versus engineering strain and uses the left-side y-axis, as indicated by the arrow 1121. The force and actuator displacement data generated during the test are recorded using a Nicolet Integra Model 10, 4 channel 1 Ms/s, 12 bit digitizer oscilloscope with the data acquisition frequency set at 40 kHz. The resulting force data may be expressed as Engineering Stress in megaPascals (MPa) using the following relationships.

Engineering Stress is defined as $$\sigma = 10^{-6} * \frac{F}{A}$$

where:

F is force in Newtons and

A is the cross-sectional area (m$^2$) of the sample, calculated as $$A = \frac{mass}{length * \rho}$$

where:

mass and length are measurements of the individual sample, as described above, and are expressed in kilograms and meters respectively.

ρ is the density of the sample, taken as 950 or 920 kg/m$^3$ for elastomers predominantly of non-hydrogenated and hydrogenated styrenic block copolymers respectively. These values are based on historical norms for similar elastomers as determined by conventional methods known to those skilled in the art (density gradient columns or application of Archimedes principle) and believed to be accurate to within 5% for the samples described in this application.

Engineering Strain (e) is defined as $$e=(L-L0)/L0=z/L0$$

where:
L0 is the gauge length (i.e., the distance between lines of grip contact when the undeformed sample is mounted in the grips. The L0 in the present example is 10 mm.
Grip position, L, is the distance between lines of grip contact during the tensile test.
Displacement, z, is defined as z=L−L0.
Engineering Strain Rate is the first time derivative of the Engineering Strain, expressed in units of $s^{-1}$. A convenient form for calculating Engineering Strain Rate is $$\frac{d\varepsilon}{dt} = \frac{v}{L0}$$

where:
v and L0 are the speed at which one grip moves relative to the other, and the sample's gauge length respectively.

High-Speed Tensile Strength is the maximum Engineering Stress borne by the sample reported to 3 significant digits.

Notched High-Speed Tensile Test

This method is used to measure the Tensile Strength of a notched sample at a relatively high strain rate, and is performed the same way as the High Speed Tensile Test described above, except that a 1 mm edge notch is cut into the sample before running. The notch is cut in the same manner as described above in the Slow Tear Test (i.e., perpendicular to the side edge of the sample). The sample is mounted with minimal slack & the notch centered between the grips.

Notched High-Speed Tensile Strength is the maximum Engineering Stress borne by the sample, reported to 3 significant digits.

EXAMPLES

Table 2 shows the formulas for making various film Samples. The S4033, JL-007, and JL-014 shown in Table 2 are hydrogenated SEEPS block copolymers available from Kuraray America, Inc. in Pasadena, Tex. S4033 is a known SEEPS block copolymer, while the JL series (e.g., JL-007 and JL-014) may be thought of as S4033-type block copolymers modified for improved processability. The JL-series of SEEPS block copolymers have a mass ratio of isoprene to 1,3 butadiene of from 46/54 to 44/56 (e.g., 45/55). The oil in Table 2 is a white mineral oil such as Drakeol 600, Hydrobrite 550, or Krystol 550. REGALREZ 1126 and REGALITE 1125 are tackifiers available from Eastman Chemical Company in Kingsport, Tenn. The PS 3190 is a polystyrene homopolymer available from NOVA Chemical Company, Canada. The material designated as "AO" is a suitable antioxidant such as Irganox 100 available from Ciba Specialty Chemicals in Switzerland.

Samples 1-11 are produced by extruding a thermoplastic composition through a slot die to form a film that is 100 mm wide and 100 nm thick. The thermoplastic composition is formed by extruding material in a Leistritz (27 mm) twin screw extruder with extended mixing sections. First, the oil and Septon polymers are mixed together, and then the polystyrene and tackifier are blended into the mixture, which is then fed into the extruder. Temperatures in the extruder typically range from 170-230° C. Subsequently, the compositions are formed into films using a ThermoFisher 20 mm single screw extruder. Temperatures in the ThermoFisher extruder typically range from 170-230° C.

TABLE 2

| Ingredient | 1 | 2 | 3 | 4 | 5 | 6 | 7 | 8 | 9 | 10 | 11 |
|---|---|---|---|---|---|---|---|---|---|---|---|
| 4033 | | | | | | | 60 | | | | 56 |
| JL-007 | 55 | 60 | 60 | 60 | | 55 | | | 60 | 56 | |
| JL-014 | | | | | 55 | | | 60 | | | |
| Oil | 15 | 20 | 20 | 16 | 15 | 15 | 20 | 20 | 20 | 31 | 31 |
| Regalrez 1126 | 15 | 10 | 15 | 16 | 15 | | | 10 | 10 | | |
| Regalite 1125 | | | | | | 15 | | | | 10 | |
| PS 3190 | 15 | 10 | 5 | 8 | 15 | 15 | 10 | 10 | 10 | 13 | 13 |
| AO | 0.05 | | | | 0.05 | 0.05 | | | | 0.1 | 0.1 |

Table 3 illustrates the time-to-fail and melt temperatures of various elastomeric film materials. Samples 1-6 and 9-10 are provided to show suitable examples of the present film. Samples 7 and 11 are provided as comparative examples to show that not all SEEPS block copolymers necessarily provide suitable tear resistance and/or processability. The time-to-fail measurements are obtained according to the Slow Tear Test and the $T_m$ values are obtained according to the DSC method. Samples 12-15 in Table 3 are formed by a two-stage compression molding procedure where the elastomer is compressed between heated platens (215° C.) and held for a dwell time of 3 minutes using shims that give a thick sheet of elastomer (approximately 2.5 mm thick) then subsequently folding and stacking the thick film and pressing without a shim and holding for a dwell time of about 30 seconds to give a film of between 80-200 μm in thickness. The percentages of the various ingredients are all weight percentages based on the weight of the film. Sample 12 is provided as a comparative example and is formed from 56% S4033, 13% PS3160, and 31% white mineral oil. Samples 13-15 include the same relative amounts of SEEPS block copolymer, polystyrene homopolymer, and mineral oil as Sample 12, but vary in the kind of SEEPS copolymer, including the $T_m$ of the polymer, used in their formation. Sample 13 is formed using 56% JL-007. Sample 14 is formed using JL-014. Sample 15 is formed using JL-013. These ingredients are added to a small batch mixer (Haake) and mixed at 50 RPM at a temperature of 210° C. for 3 minutes. Sheets are subsequently produced by pressing between heated platens held at 210° C.

TABLE 3

| Sample No. | time-to-fail (hr.) | $T_m$ (° C.) |
|---|---|---|
| 1 | 7.2 | 17.7 |
| 2 | 8.3 | 16.1 |
| 3 | 31.5 | 15.1 |
| 4 | 17.5 | 16.2 |
| 5 | 13.7 | 14.5 |
| 6 | 11.6 | 16.6 |
| 7 | 1.6 | 2.4 |
| 8 | 9.6 | 13.9 |
| 9 | 10.2 | 15.7 |
| 10 | 0.9 | 14.6 |
| 11 | 0.3 | 1.8 |
| 12 | 0.5 | −1.0 |
| 13 | 2.1 | 13.0 |
| 14 | 0.8 | 13.0 |
| 15 | 7.0 | 18.0 |

As can be seen Table 3, the Samples that include the S4033 SEEPS block copolymer fail to provide a time-to-fail of about an hour or more and/or a $T_m$ of between 10 to 20° C., whereas the samples formed from the JL-series of SEEPS block copolymers provide these desired properties.

Table 4 below illustrates the High Speed Tensile Strength and Notched High Speed Tensile Strength of film samples 13, 14, 15, and 11 from Table 3. As can be seen in Table 4, Samples 13-15 are still able to provide suitable High Speed Tensile Strength and Notched High Speed Tensile Strength in addition to slow tear resistance.

TABLE 4

| No. | Sample ID | High Speed Tensile Strength (MPa) | Notched High Speed Tensile Strength (MPa) |
|---|---|---|---|
| 11 | grf410-16-comp | 20.6 | 13.9 |
| 13 | SC1163 | 21.1 | 18.2 |
| 14 | SC1164 | 20.8 | 15.4 |
| 15 | SC1165 | 19.7 | 16.5 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Additionally, properties described herein may include one or more ranges of values. It is to be understood that these ranges include every value within the range, even though the individual values in the range may not be expressly disclosed.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An elastic film material, which resists the growth of a tear, hole, or aperture, the film material comprising an elastomeric block copolymer and having a time-to-fail of greater than 1 hour according to the Slow Tear Test, the film material having a $T_m$ of between about 10° C. and 20° C. wherein said elastomeric block copolymer comprises a SEEPS block copolymer.

2. The elastic film material of claim 1, wherein the time-to-fail is greater than 5 hours.

3. The elastic film material of claim 1, wherein the time-to-fail is greater than 24 hours.

4. The elastic film material of claim 1, wherein the film has an Effective Average Thickness of about 1 μm to 1 mm.

5. The elastic film material of claim 1, wherein the film has a basis weight of between about 20 and 140 g/m².

6. The elastic film material of claim 1, wherein the elastic film has a High-Speed Tensile Strength of between about 15 and about 22 MPa according to the High Speed Tensile Test.

7. The elastic film material of claim 1, wherein the elastic film has a Notched High-Speed Tensile Strength of between about 10 and about 20 MPa according to the Notched High-Speed Tensile Strength Test.

8. The elastic film material of claim 1, wherein the film has an L200 value of between about 0.8 and 2 MPa and a UL50 value of between 0.3 and 0.8 MPa according to the Hysteresis Test.

9. The elastic film material of claim 1, wherein the film is breathable.

10. The elastic film material of claim 1, wherein the film includes pre-formed apertures.

11. The elastic film material of claim 10, wherein the pre-formed apertures have a largest dimension in the x-y plane of the film of between about 0.2 and about 3 mm.

12. The elastic film material of claim 10, wherein the film has an open area of between about 5 and about 60%.

13. The elastic film material of claim 1, wherein the SEEPS block copolymer comprises a rubbery midblock of a hydrogenated copolymer of isoprene and butadiene.

14. The elastic film material of claim 13, wherein more than about 90% of the isoprene and butadiene in the midblock are hydrogenated.

15. The elastic film material of claim 14, wherein more than about 95% of the isoprene and butadiene in the midblock are hydrogenated.

16. The elastic film material of claim 1, further comprising a stabilizer selected from the group consisting of high molecular weight hindered phenols, multifunctional phenols, phosphates, hindered amines, and combinations thereof.

17. The elastic film material of claim 1, further comprising a bacteriostat selected from the group consisting of benzoates, phenols, aldehydes, halogen containing compounds, nitrogen compounds, and metal-containing compounds.

18. The elastic film material of claim 1, further comprising an additive selected from the group consisting of polyphenylene oxide and vinylarene polymers derived from monomers selected from the group consisting of styrene, alpha-methyl styrene, pare-methyl styrene, other alkyl styrene derivatives, vinyl toluene, and mixtures thereof.

19. The elastic film material of claim 1, further comprising a processing aid selected from the group consisting of synthetic and natural oils and hydrogenated versions thereof; naphthenic oils; paraffinic oils; olefin oligomers and low molecular weight polymers; vegetable oils; animal oils; petroleum derived waxes; and mixtures of these.

* * * * *